US00PP36686P3

(12) United States Plant Patent
Olesen

(10) Patent No.: US PP36,686 P3
(45) Date of Patent: May 20, 2025

(54) FLORIBUNDA ROSE PLANT NAMED 'Poulnap009'

(50) Latin Name: *Rosa hybrida*
Varietal Denomination: Poulnap009

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 32 days.

(21) Appl. No.: 18/831,185

(22) Filed: Sep. 5, 2024

(65) Prior Publication Data

US 2025/0107471 P1 Mar. 27, 2025

(30) Foreign Application Priority Data

Sep. 22, 2023 (QZ) ..... PBR 20231972

(51) Int. Cl.
*A01H 5/02* (2018.01)
*A01H 6/74* (2018.01)

(52) U.S. Cl.
USPC ..... Plt./142

(58) Field of Classification Search
USPC ..... Plt./101, 141, 142, 143
See application file for complete search history.

*Primary Examiner* — Susan McCormick Ewoldt

(57) ABSTRACT

A new garden rose plant of the Floribunda class which has abundant, red and white bicolor flowers and attractive foliage. This new and distinct variety has shown to be uniform and stable in the resulting generations from asexual propagation.

2 Drawing Sheets

Botanical designation: *Rosa hybrida.*
Variety denomination: 'Poulnap009'.

This application claims priority to Plant Breeder's Rights Application Number 2023/1972, which was filed at the Community Plant Variety Rights Office in the European Union on Sep. 22, 2023, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2014 and the resulting seeds were planted in a controlled environment in Fredensborg, Denmark. The new variety, named 'Poulnap009', originated as a single seedling from the stated cross.

The new variety may be distinguished from its male pollen parent and female seed parent primarily by the following characteristics. The male pollen parent plant has dark red flowers while the new variety has red and white bicolor flowers. The female seed parent plant has yellow flowers while the new variety has red and white bicolor flowers.

The objective of the hybridization of this rose variety was to create a new and distinct variety with unique qualities, such as:

1. Uniform and abundant red and white bicolor flowers;
2. Vigorous, but compact growth when propagated on its own roots;
3. Exceptional disease resistance.

This combination of qualities is not present in previously available commercial cultivars of this type, known to the inventor, and distinguish 'Poulnap009' from all other varieties of which we are aware.

As part of the rose development program, Mogens N. Olesen germinated the seeds from the aforementioned hybridization during winter of 2014 and conducted evaluations on the resulting seedlings in a controlled environment in Fredensborg, Denmark. 'Poulnap009' was selected in the spring of 2015 by the inventor as a single plant from the progeny of the aforementioned hybridization.

Asexual reproduction of 'Poulnap009' by rooted cuttings was first done by Mogens N. Olesen in the nursery in Fredensborg, Denmark in July 2015. This initial and other subsequent asexual propagations conducted in controlled environments have demonstrated that the characteristics of 'Poulnap009' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulnap009'.

Specifically illustrated in FIG. 1 of the drawings are a cluster of open flowers viewed from the side, above view of open flower, flower bud, partially opened flower, petals detached revealing reproductive flower parts, and sepals detached.

Figure 1:
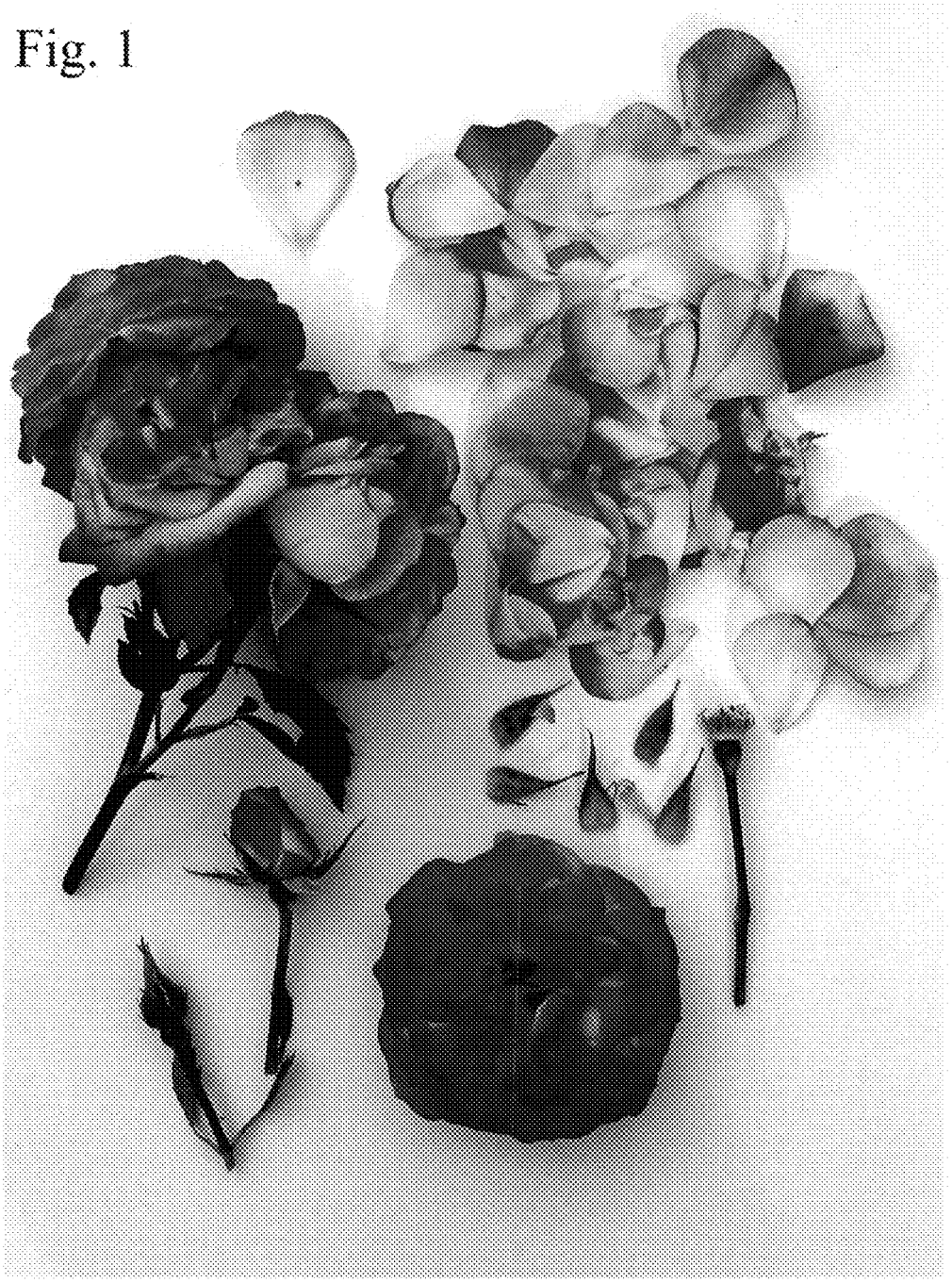
Figure 2:
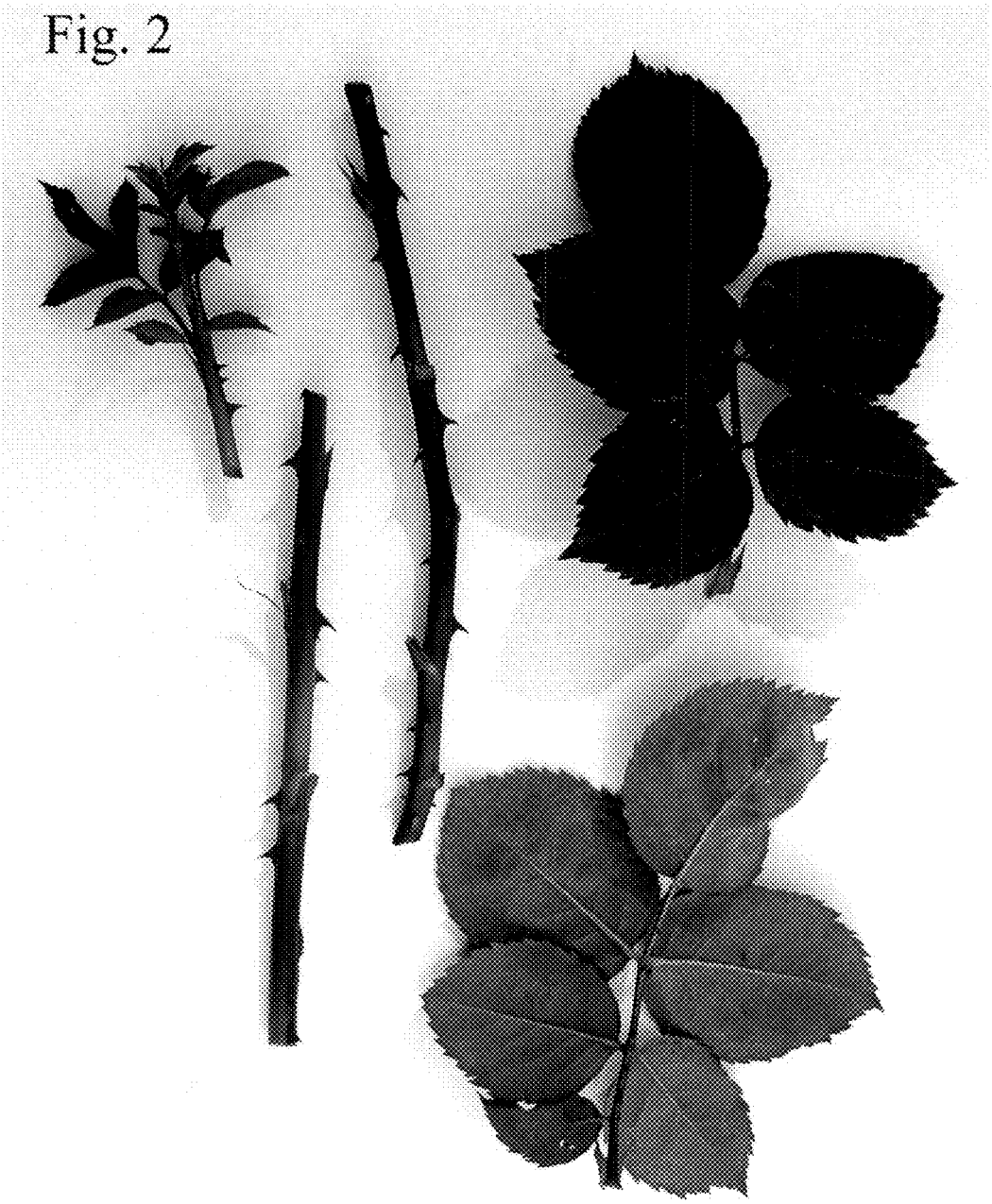

Specifically illustrated in FIG. 2 of the drawings are juvenile bare stem, juvenile leaves exhibiting anthocyanin, mature stem, and mature leaves. Plants shown are 15 months old.

DETAILED DESCRIPTION OF THE VARIETY

The following is a description of 'Poulnap009', as observed in its growth in an outdoor nursery in Odense Denmark. Observed plants are 15 months of age, and were grown on their own roots in 34 cm pots. Color references are made using The Royal Horticultural Society (London, England) Colour Chart, 2001, except where common terms of color are used.

For a comparison, several physical characteristics of the floribunda rose variety 'ANDeli', commercially known a Double Delight, described in U.S. Plant Pat. No. 3,847, are compared to the claimed plant. While 'Poulnap009' has about 65 flower petals, 'ANDeli' has 26 to 40 flower petals. The claimed plant grows to a height of about 70 cm, while 'ANDeli' grows 120 to 152 cm. Open flowers of 'Poulnap009' generally appear more red in color, while 'ANDeli' appears to be half red and half cream in color. 'ANDeli' has strong flower perfume, while the claimed plant has light scent.

FLOWER AND FLOWER BUD

Blooming habit: Continuous.

Flower bud:

*Size*.—Upon opening, 39 mm in length from base of receptacle to end of bud. Bud diameter is 15 mm.

*Bud form*.—Ucerolate.

*Bud color*.—As sepals divide petals are Red Group 46A and Yellow Group 12A.

*Sepal inner surface*.—Color: Yellow-Green Group 146C with intonations of Greyed-Red Group 182A. Surface: Lightly pubescent.

*Sepal outer surface*.—Color: Yellow-Green Group 146A with intonations of Greyed-Purple Group 183C. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—About 35 mm long, 12 mm wide.

*Receptacle*.—Texture: Smooth. Size: 7 mm in height, 8 mm wide. Color: Yellow-Green Group 146A with intonations of Greyed-Purple Group 183B. Shape: Globose.

*Pedicel*.—Surface: Smooth. Length: 35 mm on average. Diameter: 3 mm. Color: Yellow-Green Group 146B with intonations of Greyed-Purple Group 183A. Strength: Strong.

*Peduncle*.—Length: 30 to 40 mm. Diameter: About 4 mm. Color: Yellow-Green Group 146B with intonations of Greyed-Purple Group 183A. Texture: Smooth.

Flower bud development: Flower buds are borne in clusters of 5 to 7 flower buds per stem. Panicle.

Flower bloom:

*Fragrance*.—Light scent.

*Duration*.—The blooms have a duration on the plant of approximately 14 days. Petals fall cleanly away from plant after flowers have fully matured.

*Size*.—Flower diameter is about 75 mm when open. Flower depth is about 39 mm.

*Flower shape*.—Rosette, very double flower with many slightly overlapping petals of different sizes.

*Shape of flower, side view*.—The upper portion is convex. The lower portion is concave. Under normal conditions, flowers have about 65 petals. Open flowers are Red Group 46C, and Red Group 46C and White Group 155A.

Petalage: Under normal conditions, flowers have about 65 petals.

General tonality of Flower: Open flowers are Red Group 46C, and Red Group 46C with White Group 155A.

Petal color:

*Upon opening, outer petals*.—Upper surface: White Group 155A, with layers of Yellow Group 12B most intense at the basal zone. Other intonations of Red Group 56A and Red Group 53C appear towards the marginal zone. Lower surface: Shades Yellow Group 12C from the basal zone meeting shades of Red Group 56D at the middle zone. Throughout the petal are streaks Red Group 46A.

*Upon opening, inner petals*.—Upper surface: Yellow Group 13A with marginal intonations of Orange-Red Group 30A. Lower surface: Yellow Group 11A with marginal intonations of Red Group 48B.

*Basal petal spots, upon opening*.—Upper surface: Yellow Group 12B. Lower surface: Yellow Group 12C.

*After opening, outer and inner petals*.—Upper surface: Yellow Group 11C at the basal zone. Middle zone is White Group 155A. Marginal zone is shaded with Red Group 53B and Red Group 54A. Lower surface: Yellow Group 11C at the middle and basal zone. Streaks of Red Group 51B towards marginal zone.

Petals:

*Petal reflex*.—Somewhat reflexed.

*Margin*.—Entire and uniform. Moderate and light undulations.

*Shape*.—Broad and elliptic. Apex shape: Rounded. Base shape: Acute.

*Size*.—About 52 mm (l)×54 mm (w).

*Texture*.—Smooth.

*Thickness*.—Average.

Petaloids:

*Size*.—31 mm (l) by 20 mm (w) average.

*Quantity*.—About 17.

*Shape*.—Elliptical with an acute base and rounded apices. Margins have 1 or 2 clefts.

*Color*.—The upper surface is Yellow Group 11C at the basal zone, becoming White Group 155A at the middle zone with marginal intonations of Red Group 53B and Red Group 54A. The lower surface is Yellow Group 11C at the middle and basal zone with shades of Red Group 51B towards marginal zone.

Reproductive flower parts:

*Pollen*.—None observed.

*Anthers*.—Size: 3 mm in length. Color: Greyed-Orange Group 163B. Quantity: 47 on average.

*Filaments*.—Color: Yellow Group 11C. Length: 7 mm.

*Pistils*.—Length: 6 mm. Quantity: 35 on average.

*Stigmas*.—Color: Greyed-Yellow Group 162B.

*Styles*.—Color: Green-White Group 157A.

*Location of stigmas*.—Inferior in location relative to the length of the filaments and the height of the anthers.

*Hips*.—None Observed.

PLANT

Plant growth: Upright, bushy. Plants are 60 to 70 cm in height, and 70 cm wide.

Stems:

*Color of juvenile growth*.—Yellow-Green Group 144B.

*Color of mature growth*.—Yellow-Green Group 144A.

*Length*.—Canes are about 50 cm from the base of the plant to the flowering portion.

*Diameter*.—About 7 mm.

*Internodes*.—On mature canes about 30 to 45 mm between nodes.

*Surface texture*.—Young wood: Smooth. Older wood: Smooth.

Long prickles:

*Incidence*.—About 12 prickles per 10 cm of stem.

*Size*.—Average length of prickles on mature stems is 6 mm.

*Shape*.—Upper portion is convex. Lower portion is very concave.

*Color*.—Juvenile prickles: Greyed-Purple Group 184A. Mature prickles: Greyed-Purple Group 187C.

Plant foliage:

*Compound leaf*.—150 mm (l)×120 mm (w) average.

*Quantity*.—2 or 3 leaves per 10 cm of stem on average.

*Leaf bearing angle to the stem*.—45 degrees.

*Color of juvenile foliage*.—Upper side: Yellow-Green Group 1446B with intonations of Greyed-Purple Group 187B. Lower side: Yellow-Green Group 144B.

*Color of mature foliage*.—Upper side: Yellow-Green Group 147A. Lower side: Yellow-Green Group 147B.

Plant leaves and leaflets:

*Stipules*.—Size: 9 mm long, 4 mm wide. Quantity: 2 per compound leaf. Shape: Linear, slightly broad based with outward extending apices. Margins: Finely serrated. Color: Yellow-Green Group 144A.

*Petiole*.—Length: 30 mm. Diameter: 2 mm. Upper surface color: Yellow-Green Group 144A. Lower surface color: Yellow-Green Group 144A.

*Rachis*.—Length: About 50 mm. Upper surface color: Yellow-Green Group 144A with intonations of Greyed-Purple Group 183C. Lower surface color.

*Leaflet*.—Quantity: Normally 5, occasionally 7 leaflets. Margins: Serrated. Size: Terminal leaflets are about 68 mm long, 55 mm wide. Shape: Generally. Base: Rounded. Apex: Mucronate. Texture: Smooth. Thickness: Average. Arrangement: Odd pinnate. Venation: Reticulate. Glossiness: Very glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulnap009' substantially as described and illustrated herein.

* * * * *